US00PP35680P3

(12) United States Plant Patent
Zucchi et al.

(10) Patent No.: US PP35,680 P3
(45) Date of Patent: Mar. 12, 2024

(54) RASPBERRY PLANT VARIETY DENOMINATED 'OFELIA SO'

(50) Latin Name: ***Rubus idaeus* L.**
Varietal Denomination: Ofelia SO

(71) Applicant: Sant'Orsola Societa' Cooperativa Agricola, Trento (IT)

(72) Inventors: Paolo Zucchi, Tenna (IT); Sara Giacomelli, Altopiano della Vigolana (IT); Loris Osti, Tocegno (IT)

(73) Assignee: SANT'ORSOLA SOCIETA' COOPERATIVA AGRICOLA, Pergine Valsugana (IT)

( * ) Notice: Subject to any disclaimer, the term of this patent is extended or adjusted under 35 U.S.C. 154(b) by 0 days.

(21) Appl. No.: 18/073,772

(22) Filed: Dec. 2, 2022

(65) Prior Publication Data

US 2023/0116917 P1 Apr. 13, 2023

(30) Foreign Application Priority Data

Oct. 11, 2021 (QZ) ..... PBR 2021/2549

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ... A01H 5/08; A01H 5/00; A01H 6/74; A01H 6/7499
See application file for complete search history.

(56) References Cited

U.S. PATENT DOCUMENTS

PP31,991 P3 * 7/2020 Giacomelli ..... A01H 6/7499 Plt./204

* cited by examiner

*Primary Examiner* — June Hwu
(74) *Attorney, Agent, or Firm* — SILVIA SALVADORI, P.C.; Silvia Salvadori

(57) ABSTRACT

A new raspberry cultivar named Ofelia SO having good fruit colour and flavour, large and firm conical red berries is disclosed. The new cultivar has the advantages of producing fruits that are easy to pick, with a good colour and flavour and a very good shelf-life.

The new variety produces two crops per year: the fruits ripen both on previous season's cane in summer and on current season's cane in autumn.

6 Drawing Sheets

Genus and species: *Rubus idaeus* L.
Variety denomination: 'Ofelia SO'.

BACKGROUND OF THE NEW VARIETY

A new and distinct cultivar of red raspberry (*Rubus idaeus* L.) hereinafter referred to by the cultivar denomination 'Ofelia SO' is disclosed. The new variety 'Ofelia SO' was obtained from the controlled cross between the varieties 'Amaranta' (mother plant, CPVO: Application number PT9041) and SO.LR.08.25.30 (father plant, not patented).

The crossing for the new cultivar occurred in year 2017 in Altopiano della Vigolana (Trento-Italy) and it has been subject to selection in 2018, and successively tested until 2021. The characteristics of the new cultivar have been found stable and have been transmitted without change through succeeding (more than 4 years) asexual propagations by root cutting.

Plant breeder's right were applied for with the European Union on Oct. 11, 2021. 'Ofelia SO' has not been made publicly available.

SUMMARY OF THE INVENTION

The most outstanding and distinguishing characteristics of the cultivar 'Ofelia SO' are hereunder reported.

Primocane raspberry plant;
Very early to early fruit ripening on current season's cane in autumn;
Medium time fruit ripening on previous season's cane in summer;
Good fruit colour and flavour;
Very good shelf-life: average number of days is 10 days at 1.5/2.5° C.;
Firm large conical red fruits;
Easy to pick up (low adherence to plug).

The new variety produces two crops per year: the fruits ripen both on previous season's cane in summer and on current season's cane in autumn.

The new variety can be propagated by the use of suckers produced in a spawn-bed, root cutting and by use of tissue culture techniques. The root cutting technique is to be preferred.

BRIEF DESCRIPTION OF THE PHOTOGRAPHS

The new red raspberry cultivar 'Ofelia SO' is illustrated by the accompanying photographs showing typical specimens of the new variety in colour as true as reasonably possible to make the same colour illustrations of this character by conventional photographic procedures. The photographs are of plants that are from three to four months old.

DETAILED DESCRIPTION

Figure 1:
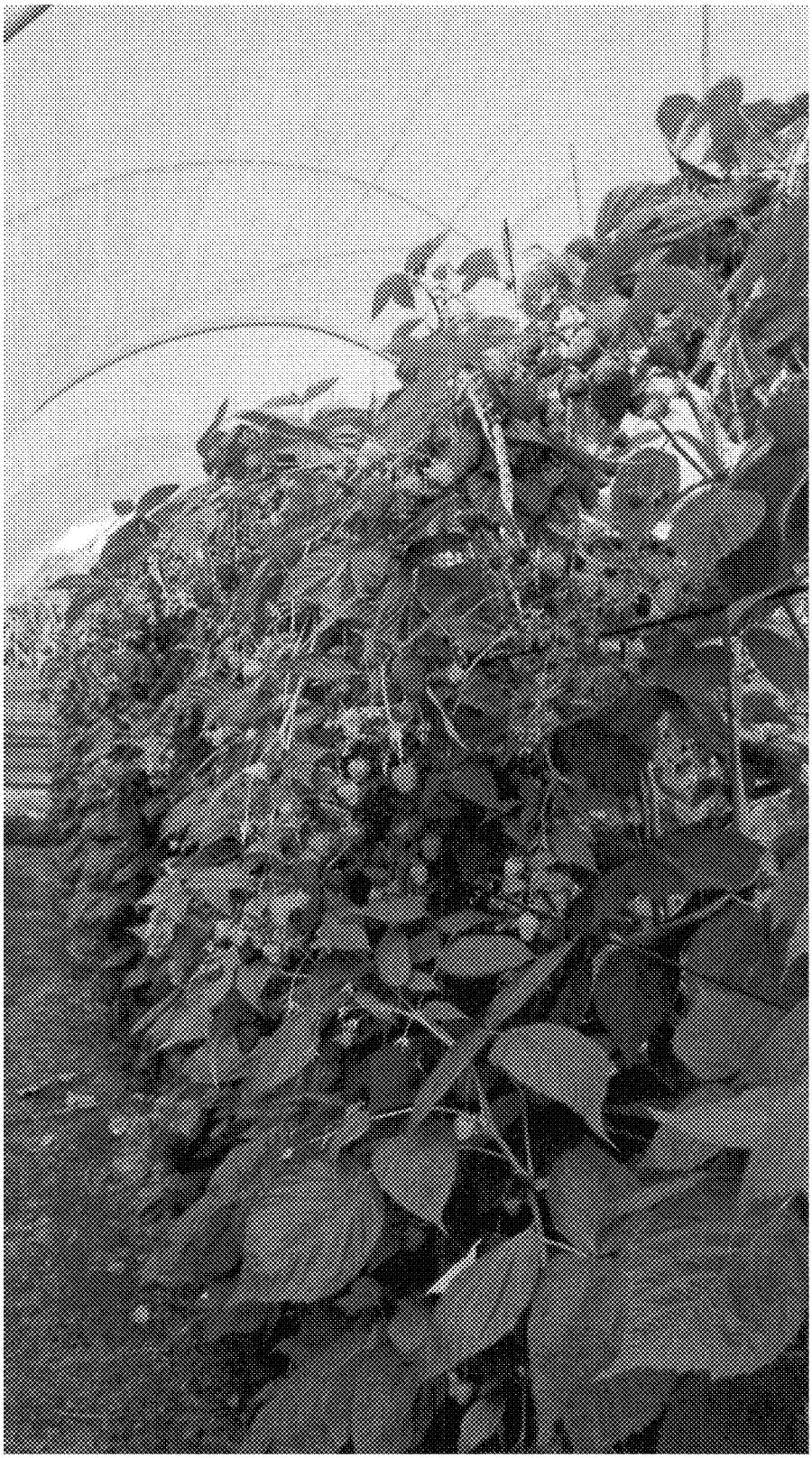
FIG. 1 is a view showing the 4-month-old raspberry plants with ripening fruit. The upright, tall plants and vigorous laterals can be appreciated.
Figure 2:
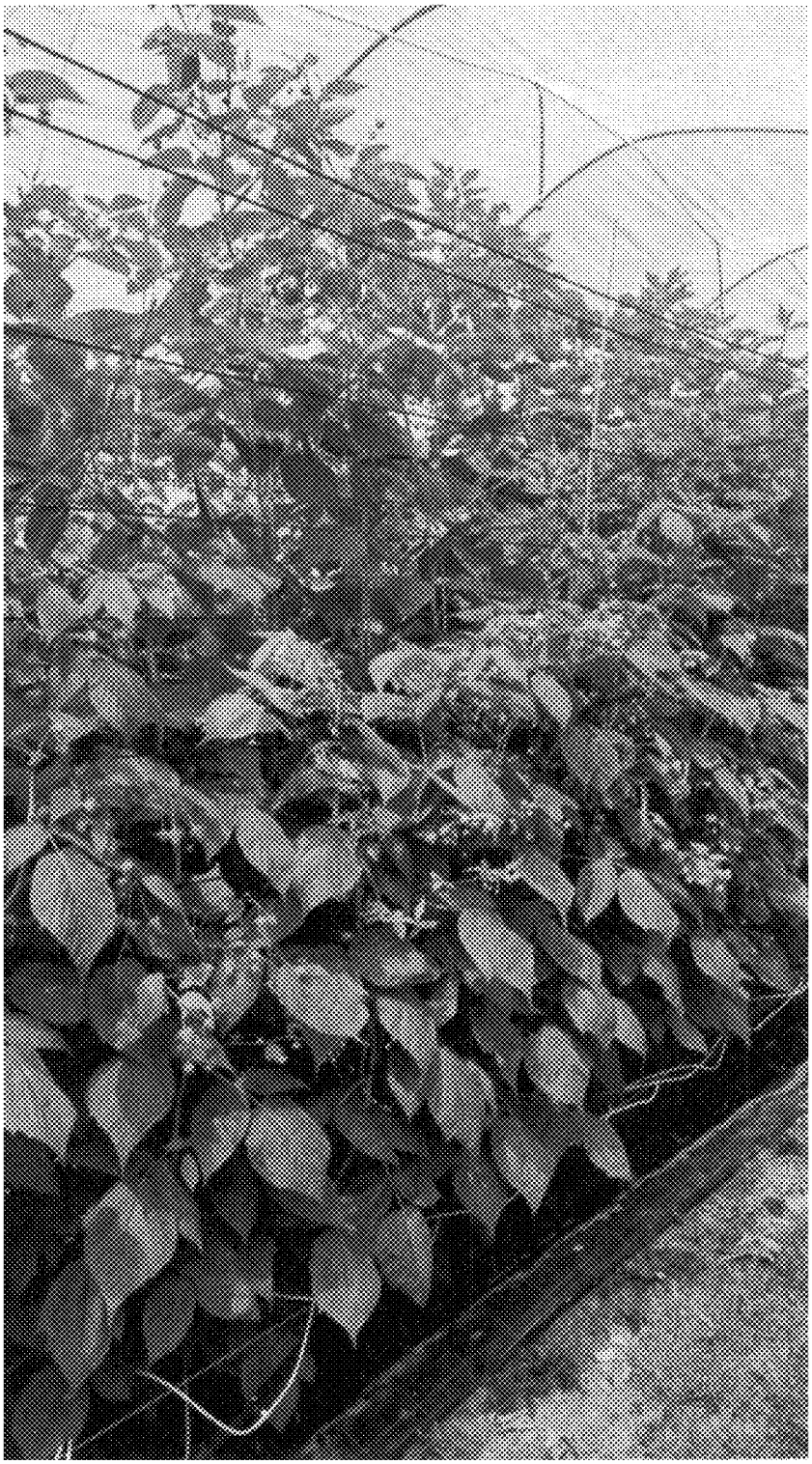
FIG. 2 is a view showing 3-month-old raspberry plants, where the leaf upper and lower surfaces can be appreciated.
Figure 3:
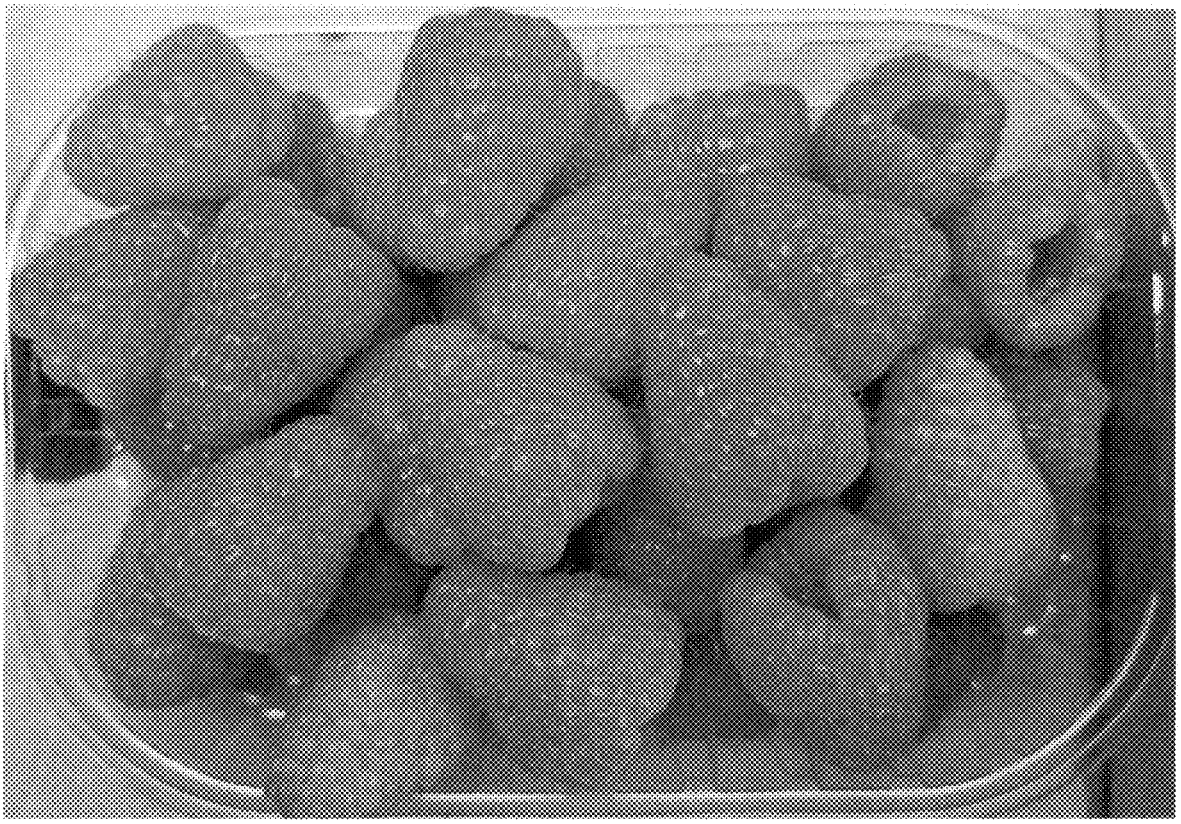
FIG. 3 is a view showing ripe 'Ofelia SO' raspberry fruits.
Figure 4:
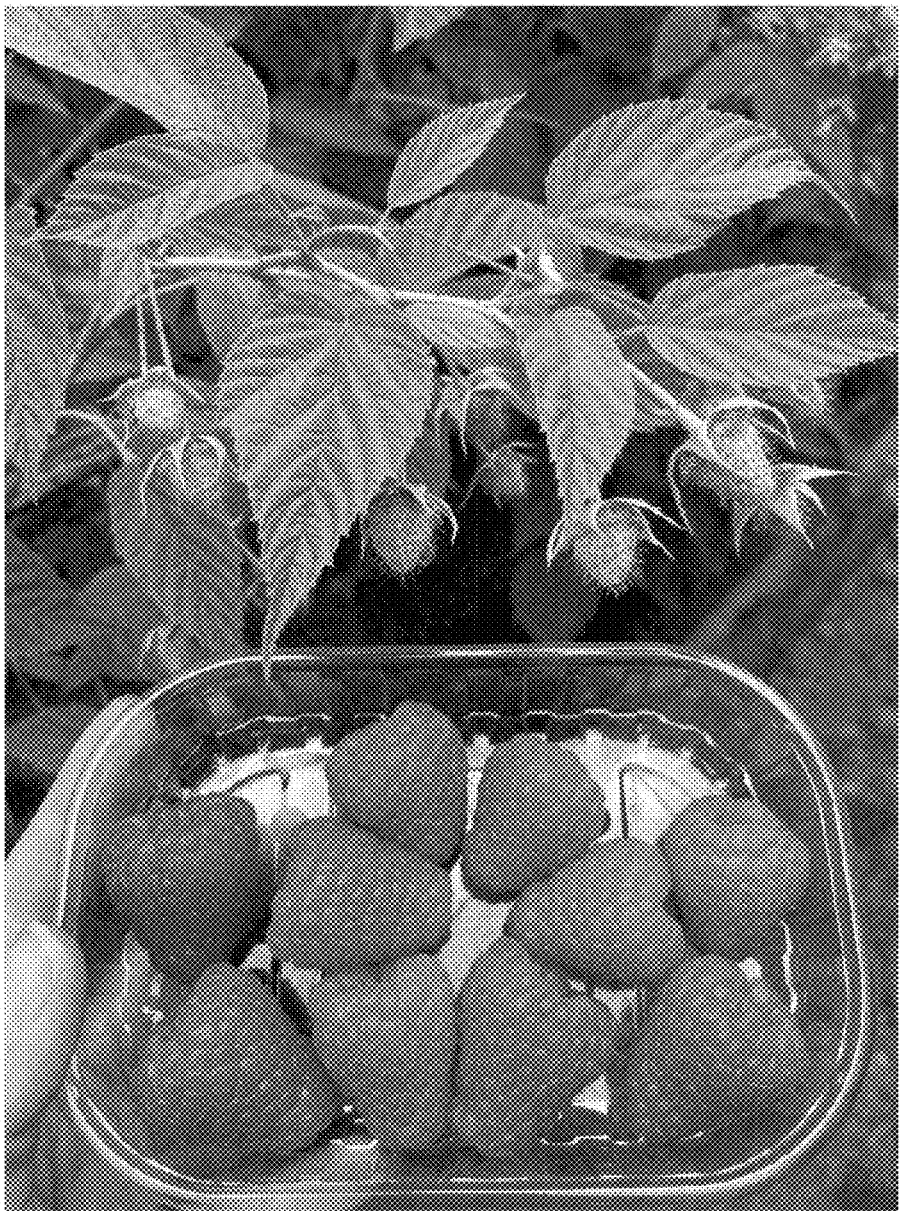
FIG. 4 is a view showing ripe fruits and ripening fruits still on the plant.
Figure 5:
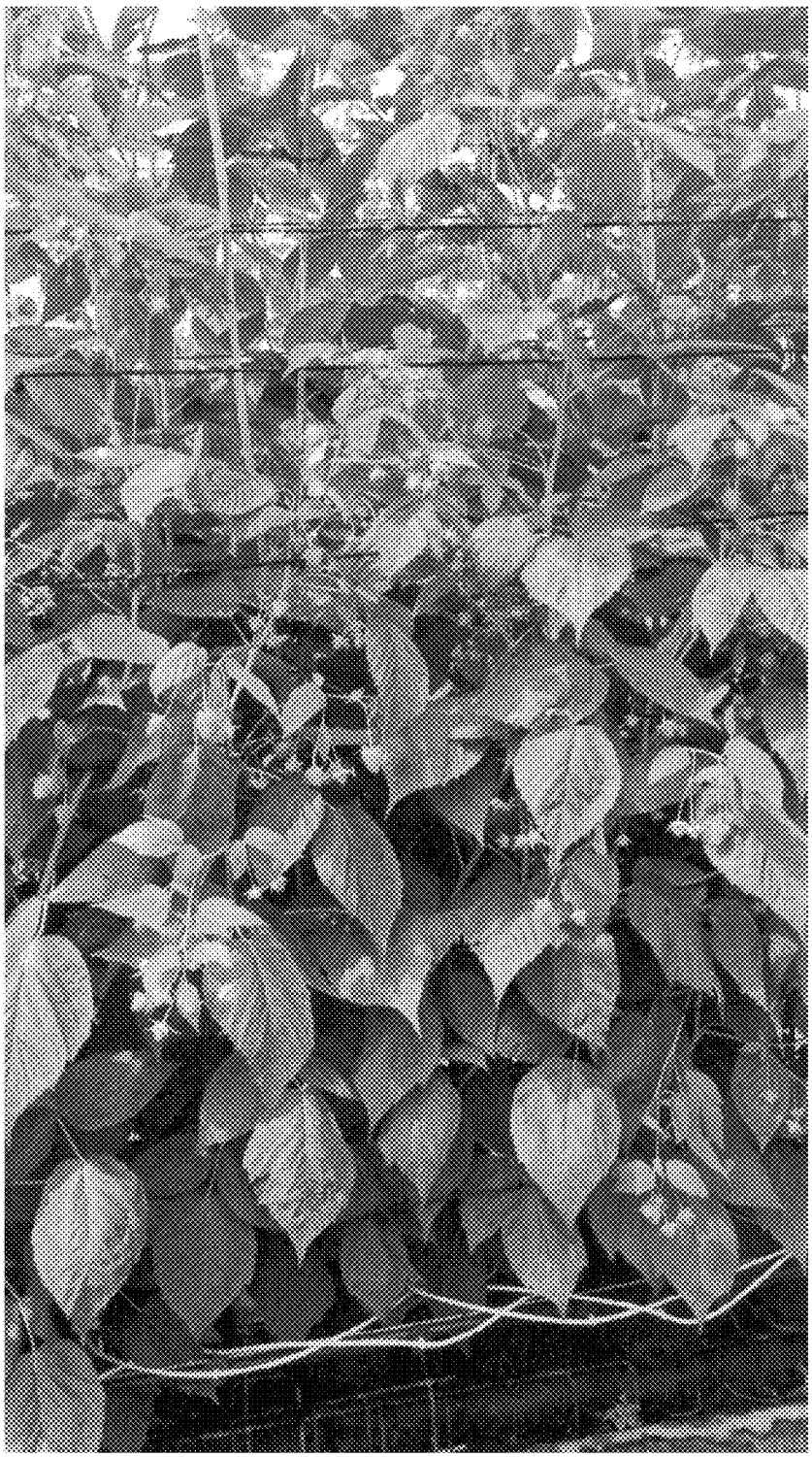
FIG. 5 is a view showing the leaves on a very vigorous plant.
Figure 6:
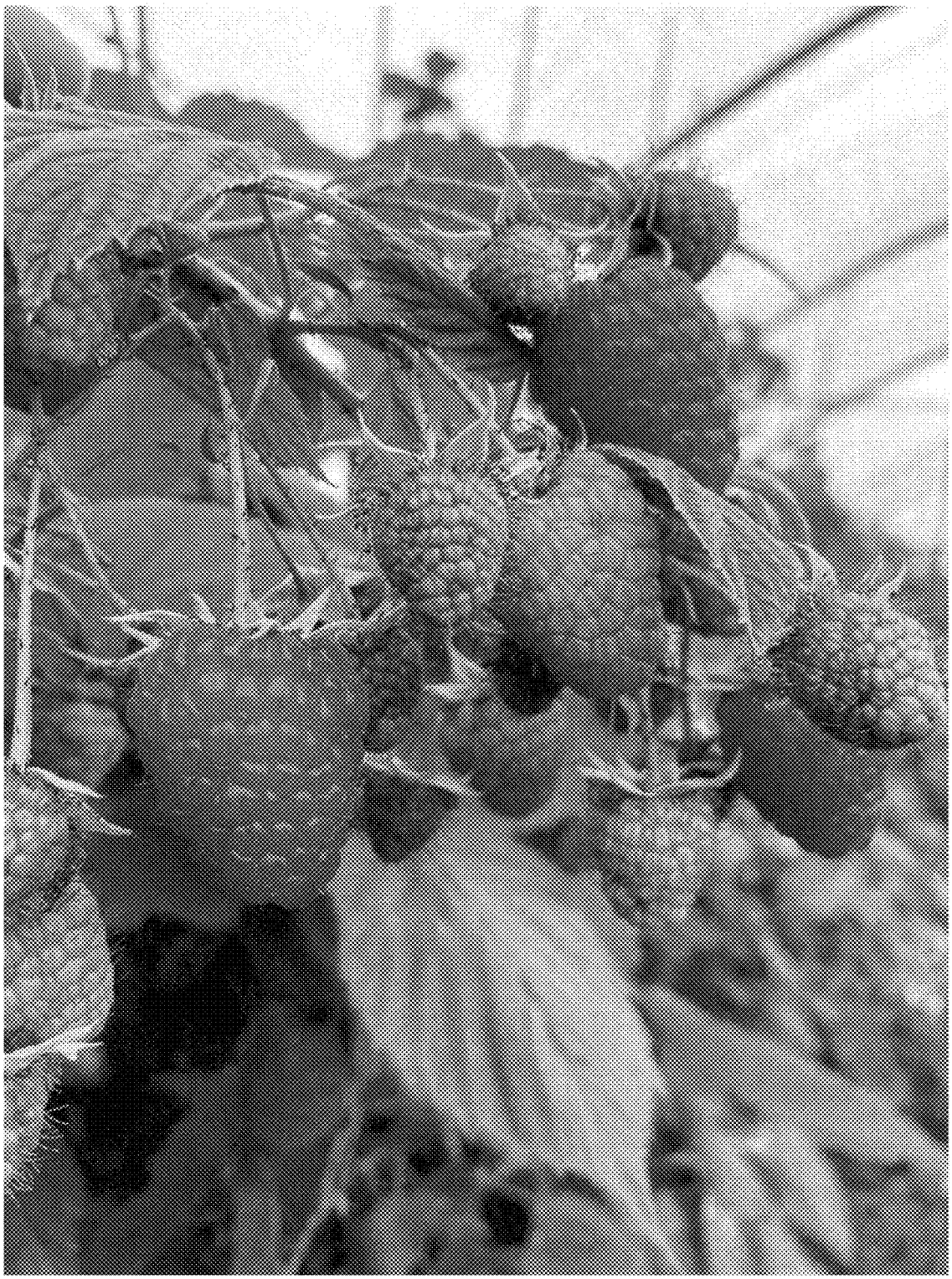
FIG. 6 is a view showing the plant with both ripening and ripe raspberry fruits.

The following detailed description set forth the distinctive characteristics of the new variety 'Ofelia SO'. The performance of the new cultivar for retention of its distinctive characteristics has been evaluated through successive asexual propagations by root cutting in the Applicant's setting in Altopiano della Vigolana, Trentino Alto Adige Region (Italy) under natural conditions in plastic covered high tunnels. The growing was in soilless using pots filled with coir as substrate.

Colour references made to R.H.S. Colour Chart of The Royal Horticultural Society of London (Edition V).

The plant assessment was performed for 4 years.

Classification:

*Family*.—Rosaceae.

*Botanical*.—*Rubus idaeus* L.

*Common name*.—Raspberry.

Parentage: 'Amaranta' x SO.LR.08.25.30.

Plant:

*General habit*.—Upright canes; medium to strong vigor; very good root system; adapted to medium winter conditions such as those at Altopiano della Vigolana (average min temperature 1° C.; average max temperature 5° C.); quite resilient to summer heat (average min temperature 13° C.; average max temperature 27° C.) suitable for being harvested both on current year's cane in autumn and on previous year's cane in summer.

*Average height*.—1.60-1.70 m.

*Spread* (*average*).—0.80 m.

*Shape*.—Conical.

*Vegetative bud length*.—Medium 5.0-6.5 mm.

Primocane:

*Length* (*average*).—1.60-1.70 m.

*Diameter* (*average*) *at* 1.0 *m height*.—0.9-1.0 cm.

*Texture*.—Smooth.

*Internode length* (*average*) *at* 1.0 *m height*.—5-6 cm.

*Number of fruiting laterals per cane* (*average*).—9-11.

*Number of current season's shoots*.—Medium.

*Young shoot colour*.—*RHS:144A The anthocyanin coloration on the very young shoot apex during rapid growth is weak.

*Dormant cane colour*.—*RHS:185A.

*Cane colour*.—*RHS: N144C.

*Spines*.—Present.

Floricane:

*Dormant cane colour*.—*RHS: 72A.

*Fruiting lateral attitude in summer*.—Semi erect.

Spines:

*Shape*.—Conical.

*Size* (*average*).—1.0-1.5 mm.

*Density* (*average*) *at* 1.2 *m*.—2.1-2.4 per $cm^2$.

*Colour*.—*RHS N77A.

Foliage:

Leaves:

*Shape*.—Compound; odd-pinnate and subdivided in 3 cordate and serrate.

*Profile in cross section*.—Slightly convex.

*Rugosity*.—Weak to medium.

*Complete leaf*.—Length: 33.4 cm. Width: 29.8 cm. Number of leaflets: 3.

*Upper surface colour*.—*RHS 141B.

*Lower surface colour*.—*RHS 147D.

*Lateral leaflets*.—Specular.

*Lateral leaflets position*.—Free.

*Lateral leaflets average size*.—Length: 13.9 cm. Width: 9.1 cm.

*Lateral leaflets apex shape*.—Pointed.

*Lateral leaflets base shape*.—Ovate.

*Lateral leaflets margin type*.—Serrate.

*Terminal leaflets average size*.—Size: Length: 16.4 cm. Width: 11.4 cm.

*Terminal leaflets apex shape*.—Pointed.

*Terminal leaflets base shape*.—Cordate.

*Terminal leaflets margin type*.—Serrate.

Petiole:

*Average length*.—10.1 cm.

*Average diameter*.—0.5 cm.

*Colour*.—*RHS 143D.

Inflorescence:

*Average length*.—48.8 cm.

*Average diameter*.—34 cm.

Flowers:

*Number per plant* (*average*).—256.

*Length* (*average*).—9.56 mm.

*Diameter* (*average*).—31.35 mm.

*Diameter* (*receptacle*).—10.50 mm.

*Shape*.—Pentagonal.

*Petal colour* (*upper surface*).—*RHS: NN155B.

*Petal colour* (*lower surface*).—*RHS: NN155C.

*Petal number* (*average*).—5.

*Petal shape*.—Obovate. — apex: rounded. — Base: cuneate. — Margin: entire.

*Sepal number* (*average*).—5. — colour (upper surface): *RHS: 144A. — colour (lower surface): *RHS: 144C. — length (average): 1.3 cm. — width (mid part): 0.6 cm.

*Fragrance*.—Absent.

*Blooming*.—— Primocane: July-August. Primocane's time of cane emergence is medium. — Floricane: April-May. Floricane's time of vegetative bud burst is medium. Floricane's average length is 85 cm and the number of lateral branches per cane is 14-16.

*Pedicel length* (*average*).—2.5 cm.

*Pedicel spines*.—Present, many.

*Peduncle*.—Average length: 10.5 cm.

*Peduncle surface texture*.—Smooth.

*Peduncle anthocyanin coloration and intensity*.—Present, very weak.

Fruit:

*Predominant shape*.—broad conical.

*Weight*.—5.6 g.

*Size*.—Length 2.3 cm. width 2.4 cm.

*Colour of ripe fruit*.—*RHS 45D.
*Colour of immature fruit*.—*RHS 41D.
*Firmness*.—Firm (0.045 kg).
*Drupes per fruit* (*average*).—135.
*Drupe size*.—Length: 3.9 mm. Width: 3.6 mm. Depth: 6.0 mm.
*Glossiness*.—Medium to high.
*Adherence to plug*.—Low.
*Titratable acidity*.—31.52 meq NaOH/hg.
*Soluble solids*.—8.6° Brix.
*Harvest season*.—— Primocane: August to October. — Floricane: Half June-end of July.
*Autumn yield*.—5.8 Kg/m (4 plants/m).
*Summer yield*.—4.6 kg/m (4 plants/m).
*Main bearing type*.—Both on current year's cane in autumn and on previous year's cane in summer.
*Use/market*.—suitable for consumption as high grade fresh fruits and also amenable to processing.
*Keeping quality*.—The fruit colour is stable during the storage the high glossiness makes it attractive.
*Storage capacity* (*shelf life*).—Very good shelf-life.
*Shipping quality*.—Good; the attitude to storability permits shipping.

Reproductive organs:
*Pistil number per flower* (*average*).—146.
*Pistil size* (*average*).—5.44 mm.
*Stamen number per flower* (*average*).—130.
*Stamen size* (*average*).—5.20 mm.

Seeds:
*Size* (*average*).—Length: 2.81 mm. width: 1.66 mm.
*Shape*.—Kidney-shaped.

COMPARISON WITH PARENTAL AND COMMERCIAL CULTIVAR

TABLE 1

Comparison table between 'Ofelia SO' variety and commercial cultivar Dafne)
(U.S. Plant patent application no. 16/350,828, PP31,991)

| Characteristic | 'Dafne' | 'Ofelia SO' |
|---|---|---|
| fruit color | Dark Red | Red |
| Plant (size/vigor) | Average height/ Strong vigor | Small to average height/Medium to strong vigor |

TABLE 1-continued

Comparison table between 'Ofelia SO' variety and commercial cultivar Dafne)
(U.S. Plant patent application no. 16/350,828, PP31,991)

| Characteristic | 'Dafne' | 'Ofelia SO' |
|---|---|---|
| Fruit: firmness | Firm | Firm |
| Fruit: size | Very big | Big |
| Fruit glossiness: | High | Medium to high |
| Fruit shape | Broad conical | Broad conical |
| Spine shape | Shark fin | Conical |
| Fruit picking | Easy | Easy |

TABLE 2

Comparison table with parental cultivars: female parent

| Characteristic | 'Amaranta' (female parent) | 'Ofelia SO' |
|---|---|---|
| Fruit color | Light red | Red |
| Fruit shape | Elongated conical | Broad conical |
| Plant vigour | Weak to medium | Weak to medium |
| Fruit firmness | Firm to very firm | Firm |
| Fruit glossiness | Medium | Medium to high |
| Fruit picking | Very easy | Easy |

TABLE 3

Comparison table with parental cultivars: male parent

| Characteristic | 'SO.LR.08.25.30' (male parent) | 'Ofelia SO' |
|---|---|---|
| Fruit color | Strong red | Red |
| Fruit shape | Conical | Broad conical |
| Plant vigor | Weak | Weak to medium |
| Spines | Thin medium dense | Medium sparse |
| Fruit firmness | Firm to very firm | Firm |
| Fruit glossiness | Medium to high | Medium to high |
| Fruit size | Medium to big | Big |
| Fruit picking | Slight difficult | Easy |

What is claimed:

1. A new and distinct cultivar of raspberry plant named 'Ofelia SO' as substantially herein shown and described.

* * * * *